(12) United States Patent
Saksena et al.

(10) Patent No.: US 7,897,724 B2
(45) Date of Patent: Mar. 1, 2011

(54) SOLID PHASE FMOC CHEMISTRY PROCESS TO PREPARE PEPTIDES

(75) Inventors: Divya Lal Saksena, Mumbai (IN); Shrikant Mishra, Mumbai (IN); Chandrakesan Muralidharan, Tamil Nadu (IN); Nilesh Patil, Navi Mumbai (IN); Nikhil Umesh Mohe, Mumbai (IN); Mandar Ravindra Maduskar, Mumbai (IN)

(73) Assignee: USV, Ltd., Mumbai (IN)

( * ) Notice: Subject to any disclaimer, the term of this patent is extended or adjusted under 35 U.S.C. 154(b) by 857 days.

(21) Appl. No.: 11/729,047

(22) Filed: Mar. 27, 2007

(65) Prior Publication Data

US 2007/0249806 A1    Oct. 25, 2007

Related U.S. Application Data

(63) Continuation-in-part of application No. 10/592,118, filed on Aug. 15, 2007.

(51) Int. Cl.
*C07K 1/06*    (2006.01)
(52) U.S. Cl. ......... 530/336; 530/333; 530/334; 530/335; 530/329
(58) Field of Classification Search .......... None
See application file for complete search history.

(56) References Cited

U.S. PATENT DOCUMENTS

2004/0249121 A1 * 12/2004 Tovi et al. ............... 530/307

FOREIGN PATENT DOCUMENTS

WO    WO 03/093302    * 11/2003

* cited by examiner

*Primary Examiner* — Anish Gupta
(74) *Attorney, Agent, or Firm* — Pharmaceutical Patent Atty's LLC

(57) ABSTRACT

The present invention relates to an improved process for the preparation of $N^6$-(aminoiminomethyl)-$N^2$-(3-mercapto-1-oxopropyl)-L-lysylglycyl-L-α-aspartyl-L-tryptophyl-L-prolyl-L-cysteinamide, cyclic(1→6)-disulfide of formula (1), which involves assembling a peptide chain comprising of six amino acids and a thioalkyl carboxylic acid in a required sequence on a solid support to obtain a peptide bound resin of formula (2), capping the free amino groups after each coupling, cleaving Dde group in the peptide of formula (2) from the solid support to obtain peptide-solid support of formula (3), guanylating the peptide of formula (3) at ε-lysine-$NH_2$ in an organic solvent to obtain peptide-solid support of formula (4), cleaving and deprotecting all groups in the peptide of formula (4) from the solid support to obtain peptide-amide formula (5), oxidizing the SH-peptide of formula (5) with an appropriate oxidizing agent to obtain the crude peptide-amide of formula (1) and purifying the crude peptide-amide of formula (1) by chromatographic technique. The solid support is either resin or a cellulose support like cotton, gauze, fabric, paper and perloza beads. The described process is simple, easy, environment friendly, takes lesser time and more cost effective.

17 Claims, 7 Drawing Sheets

Figure 1:
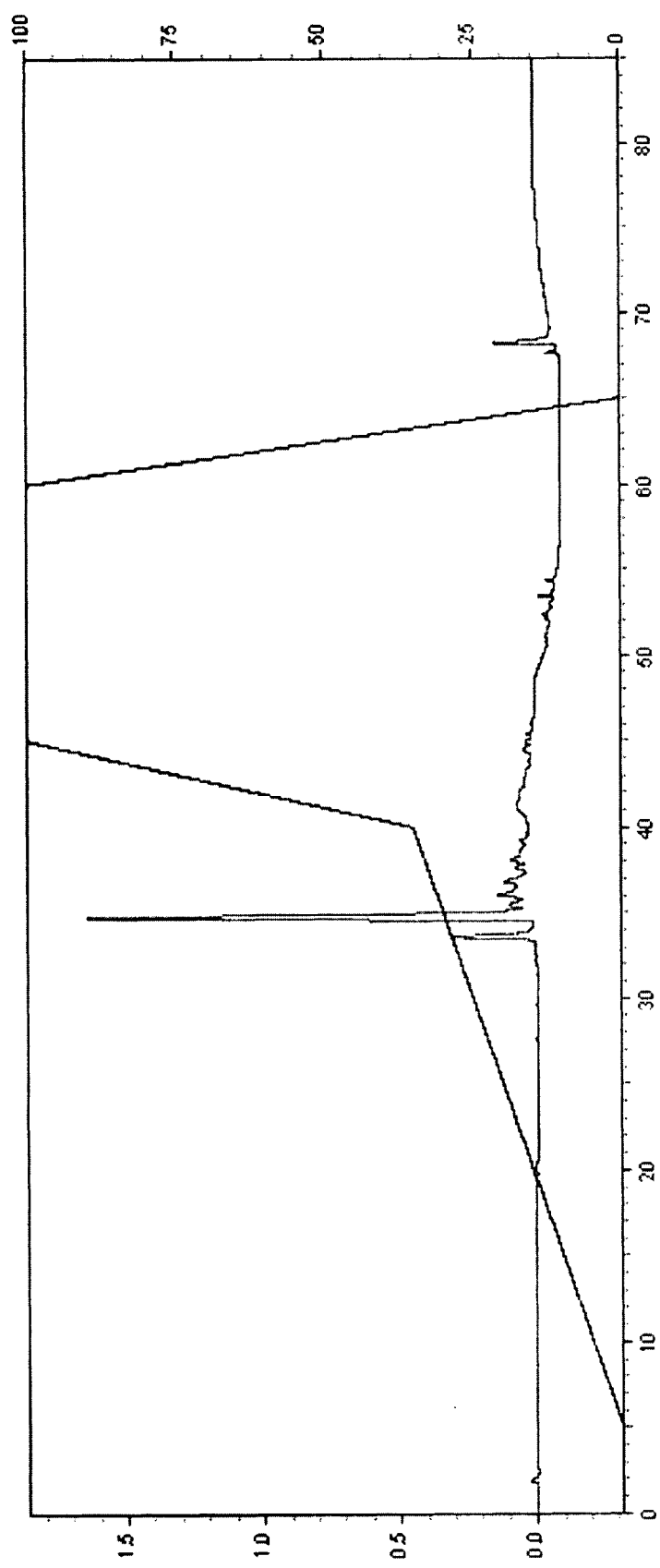

*Mass Spectra of peptide of formula 1*

_US 7,897,724 B2_

SOLID PHASE FMOC CHEMISTRY PROCESS TO PREPARE PEPTIDES

CROSS-REFERENCE TO RELATED PATENT APPLICATIONS

This application is a continuation-in-part of currently pending U.S. application Ser. No. 10/592,118, filed Aug. 15, 2007, the contents of which are here incorporated by reference.

TECHNICAL FIELD

The present invention relates to an improved process for the preparation of $N^6$-(aminoiminomethyl)-$N^2$-(3-mercapto-1-oxopropyl)-L-lysylglycyl-L-α-aspartyl-L-tryptophyl-L-prolyl-L-cysteinamide cyclic(1→6)-disulfide of formula (1) using solid phase Fmoc-chemistry.

BACKGROUND

U.S. Pat. No. 5,318,899 describes $N^6$-(aminoiminomethyl)-$N^2$-(3-mercapto-1-oxopropyl)-L-lysylglycyl-L-α-aspartyl-L-tryptophyl-L-prolyl-L-cysteinamide, cyclic (1→6)-disulfide of the formula (1) as a therapeutic agent for the treatment of, and prevention of, platelet-associated ischemic disorders. It binds to the platelet receptor glycoprotein (GP) of human platelets and inhibits platelet aggregation. Platelet aggregation is mediated by GP complex on the surface of the platelet membrane. It exists on the surface of unstimulated platelets in an inactive form. When platelets are activated by adhesion and the physiological agonists, the GP also becomes activated such that it becomes a receptor for fibrinogen, von Willebrand Factor (vWF), and fibronectin. However, it is the binding of fibrinogen and/or vWF that is believed to be principally responsible for platelet aggregation and thrombus formation in vivo. This teaches that substances, which specifically inhibit the binding of fibrinogen or vWF to GP, inhibit platelet aggregation and could be candidates for inhibiting thrombus formation in vivo (Eric J. Topol, Tatiana V. Byzova, Edward F. Plow and The Lancet; Vol 353; Jan. 16, 1999; pg 227-231). This article describes the compound having platelet aggregation inhibition activity but does not teach the method to synthesize the molecule.

Antagonists of platelet glycoprotein IIb/IIIa have an approved role in reducing the extent of thrombotic complications leading to myocardial damage during percutaneous coronary interventions (PCI).

Compound of formula (1) is a disulphide looped cyclic heptapeptide containing six amino acids and one mercaptopropionyl(desamino cysteinyl) residue. The disulfide bridge is formed between the cysteine amide and the mercaptopropionyl moieties. It is known to be produced by solution-phase peptide synthesis and purified by preparative reverse phase liquid chromatography and lyoplilized (www.fda.gov/cder/foi/label/1998/207181bl.pdf).

In terms of peptide synthesis methodology, two major synthetic techniques dominate current practice. These are synthesis in solution (homogeneous phase) and synthesis on solid phase (heterogeneous phase). But solution phase route is more cumbersome as compared to the solid phase route as after each coupling the peptide formed has to be isolated, whereas in the solid phase synthesis, the excess reagents and by-products are washed off by simple filtration. In both, the desired peptide compound is prepared by the step-wise addition of amino acid moieties to a building peptide chain.

U.S. Pat. Nos. 5,958,732 and 5,318,899 claim about recombinant techniques to synthesize peptides like $N^6$-(aminoiminomethyl)-$N^2$-(3-mercapto-1-oxopropyl)-L-lysylglycyl-L-α-aspartyl-L-tryptophyl-L-prolyl-L-cysteinamide, cyclic(1→6)-disulfide of the formula (1). The peptide obtained by this recombinant process is modified by solution phase synthesis for conversion of lysine residue to homoarginine residue. These patent documents also claim solid phase synthesis using Boc chemistry and the subject matter of these patents is fundamentally different from the present invention.

As compared to Boc-chemistry, Fmoc-chemistry based synthesis utilizes a mild procedure and because of the base lability of Fmoc group, acid-labile side-chain protecting groups are employed providing orthogonal protection. The rationale for use of protecting groups is that the energy of breaking a bond of a protecting group is lower than any other group.

U.S. Pat. Nos. 5,686,566, U.S. Pat. No. 5,686,567, U.S. Pat. No. 5,686,569, U.S. Pat. No. 5,686,570 and U.S. Pat. No. 5,756,451 deal with different PAI's in their salt or other forms of the compound of formula (1) but do not teach the process for its preparation using Fmoc solid phase synthesis.

Likewise, U.S. Pat. No. 5,759,999, U.S. Pat. No. 5,786,333, U.S. Pat. No. 5,770,564, U.S. Pat. No. 5,807,825, U.S. Pat. No. 5,807,828, U.S. Pat. No. 5,843,897, U.S. Pat. No. 5,968,902. and U.S. Pat. No. 5,935,926 describe the method of treating platelet-associated disorders and the process for the preparation of peptide amide of formula (1) using boc chemistry.

U.S. Pat. No. 5,344,783 and U.S. Pat. No. 5,851,839 deal with methods for selecting and identifying Platelet Aggregation Inhibitors (PAI) and disclose boc chemistry for the preparation of peptide amide of formula (1).

U.S. Pat. No. 5,780,595 claims antibodies specific to PAI's and also discloses boc chemistry for the preparation of the peptide amide of formula (1).

The Fmoc route of synthesis of various other peptides is well-known in prior art and several documents are available for their preparation. However there is a definite need to develop a process for the preparation of compound of formula (1) which is economical, involves minimal steps and also eco-friendly.

As explained earlier, Fmoc-chemistry based synthesis utilises a mild procedure and because of the base lability of Fmoc group, acid-labile side-chain protecting groups are employed providing orthogonal protection. The protecting groups used in Fmoc chemistry are based on the tert-butyl moiety: tert-butyl ethers for Ser, Thr, tert-butyl esters for Asp, Glu and Boc for Lys, His. The trt and acm groups have been used for the protection of Cys. The guanidine group of Arg and Har is protected by Mtr, Pmc or Pbf. Most of the Fmoc-amino acids derivatives are commercially available. However, a problem exists in the art for the preparation of some amino acid analogs like peptides containing homoarginine as well as cyclic peptide compounds based on disulfide links, because separate operations are required before purifying the end product, which increases expense and may affect final product purity and yield. Fmoc-homoarginine residue if purchased commercially for use in the assembly of the chain becomes expensive. Alternatively in the peptide assembly, the Har unit is built by guanylation of the lysine residue at the α-$NH_2$ which has been demonstrated to obtain vasopressin analogues for the evaluation of its biological activity (Lindeberg et al, Int. J. Peptide Protein Res. 10, 1977, 240-244).

CN1500805 discloses preparation of Eptifibatide comprising: eliminating Fmoc protection of Fmoc-Rink Amide AM resin to obtain $H_2N$-Rink Amide AM resin; connecting various protective amino acids successively to obtain corresponding resin; eliminating Fmoc-protection radical and Kaiser test to detect reaction procedure; preparing S-triphenyl mercapto propionyl-N, N-ditert butyl oxycarbonyl-homoarginine with lysine; grafting S-triphenyl mercapto propionyl-N,N-ditert butyl oxycarbonyl-homoarginine; eliminating side chain protecting radical and resin to reduce into coarse product; and cyclization, oxidation, HPLC tracking purification to obtain pure product.

WO 03/093302 discloses the synthesis of the peptide of formula (1) using Fmoc-α-nitrogen protected Cα-carboxamide cysteine. It describes the attachment of the first amino acid, cysteine in the protected form to the solid support 4-methoxytrityl polystyrene resin through its thiol side chain, followed by removing the α-nitrogen protecting group and assembling the peptide on the said resin. However, the process uses the solid support-4-methoxytrityl polystyrene resin which is not a common commercial embodiment and also the Fmoc-α-nitrogen protected Cα-carboxamide cysteine is not commercially available. This enables the process having increased number of steps and also expensive with respect to the process of the present invention. The cleavage conditions utilize ethanedithiol, which makes the process highly toxic and non-environment friendly requiring the use of expensive scrubbers. The use of Fmoc-homoarginine residue in the assembly of the chain is mentioned, which if purchased commercially, also makes the process very expensive. Overall, the process claimed in this document is different from the process claimed in the present invention. In addition the process of WO 03/093302 is associated with certain limitations, which has been overcome by providing suitable modifications in the process steps of the present invention.

A considerable number of known, naturally occurring small and medium-sized cyclic peptides as well as some of their synthetic derivatives and analogs possessing desirable pharmacological properties have been synthesized. However, wider medical use is often hampered due to complexity of their synthesis and purification. Therefore, improved methods for making these compounds in simple, lesser steps and at lesser cost are desirable and it is the need of the industry and mankind.

The purity and yield of the peptide are important aspects of any route of synthesis. Yield, represented by the relative content of the pharmacologically active compound in the final product, should be as high as possible. Purity is represented by the degree of presence of pharmacologically active impurities, which though present in trace amounts only, may disturb or even render useless the beneficial action of the peptide when used as a therapeutic agent. In a pharmacological context both aspects have to be considered. As a rule, purification becomes increasingly difficult with larger peptide molecules. In homogeneous (solution) phase synthesis (which is the current method of choice for industrial production of larger amounts of peptides) repeated purification required between individual steps provides a purer product but low yield. Thus, improvements in yield and purification techniques at the terminal stages of synthesis are needed. The present invention is an industrially feasible solid phase synthesis and is a novel process to yield a high purity product with enhanced yield.

Mutulis, F et al. discloses the use of a solid support system comprising cotton for multiple peptide synthesis (Journal of Combinatorial Chemistry, 5(1), January/February 2003).

Prior art describes the use of HOBT and DIC for activation of amino acids, which leads to the formation of Benzotriazole ester. However, a major drawback in using this procedure is that the preparation of the OtBu ester itself takes about 20 min and also the reaction has to be carried out at 0° C. The step-wise introduction of Nα-protected amino acids in SPPS normally involves in situ carboxyl group activation of the incoming amino acid or the use of pre-formed activated amino acid derivatives. In recent years, aminium and phosphonium based derivatives (HBTU, TBTU, Py Boc. and HATU) have become the preferred tools for in situ carboxyl activation. They have been shown to give superior results in terms of both coupling efficiency and suppression of enantiomerization. (Fmoc Solid Phase Peptide Synthesis by Chan W. C. and White P. D., Oxford University Press, 2000, p. 41-74) Use of HBTU provides high yield and high purity. It saves time in the activation step with no cooling required. Double coupling is also not required for Mpr(Acm)-OH.

Most of the Fmoc-amino acids derivatives are commercially available. However, a problem exists in the art for the preparation of some amino acid analogs like peptides containing homoarginine as well as cyclic peptide compounds based on disulfide links, because separate operations are required before purifying the end product, which increases expense and may affect final product purity and yield. Fmoc-homoarginine residue if purchased commercially for use in the assembly of the peptide chain becomes very expensive. Alternatively the peptide assembly can be built using lysine followed by guanylation of the lysine residue at the α-NH$_2$ (Lindeberg et al., Int. J. Peptide Protein Res. 10, 1977, 240-244).

Fmoc-Lys(Boc)-OH is recommended for the routine preparation of Lysine containing peptides. For carrying side-chain modification of the Lys residue on the solid support, derivatives such as Fmoc-Lys(Mtt)-OH, Fmoc-Lys(ivDde)-OH, Fmoc-Lys(Mmt)-OH, Fmoc-Lys(Dde)-OH can be used since their respective side-chain protecting groups can be removed selectively on the solid-phase. (Rohwedder, B., et al.; Tetrahedron Letters, 39(5), 5 Mar. 1998, pp 1175-78 & Chhabra, S. R., et al.; Tetrahedron Letters, 39(12), 19 March 1998, pp 1603-06).

Oxidative cyclization of protected or non-protected sulfhydryl groups with formation of disulfide structures is usually carried out as the final synthetic step, the reason being substantial thermal and chemical lability of the disulfide linkage. In few cases it is also carried out before cleavage of the peptide molecule from the solid support. The oxidation of open-chain peptides containing free and/or certain types of protected sulfhydryl groups with iodine in, e.g., methanol or acetic acid is further explained in the CRC Handbook of Neurohypophyseal Hormone Analogs, Vol. 1, Part I: Jost, K., et al. Eds., CRC Press, Boca Raton, Fla. 1987, p. 31. Iodine, however, is not without drawbacks as a cyclization agent. For instance, tryptophan moieties present in peptide substrates are at risk of being iodinated, making the balance between full conversion of starting materials and minimizing side reactions a delicate one, which, in turn, impacts product purity. Tam (Tam J. P. et al., 1990, J. Am. Chem. Soc., Vol. 113, p. 6657) has demonstrated that the use of 20-50% solutions of DMSO in a variety of buffer systems greatly promotes disulfide bond formation in comparison with other methods such as aerial oxidation. DMSO is also found to greatly reduce and in some instances, suppress completely, the aggregation and precipitation of peptides that occurred using other oxidative procedures. Thus, the yield and purity of the disulfide looped peptide oxidized by DMSO is much higher as compared to other known methods. In the present invention this aspect has been rightfully tackled by not opting for Iodine route for oxidative cyclization. Thus the process steps of deprotection followed by oxidation of guanylated peptide amide adopted in the present invention yields crude peptide amide comprising compound of formula (1) of enhanced purity and yield.

Finally purification of the crude peptide result in enhanced yield of the final pure peptide.

Another complicating factor in known routes of synthesis is the possibility of interaction between the desired cyclic disulfide and inorganic sulfur compounds used for reducing excess iodine at the end of the reaction, such as sodium dithionite or sodium thiosulfate. Such reducing sulfur-containing compounds may interact with the disulfide linkage, which is sensitive to nucleophilic attack in general. As the process of the present invention has avoided use of iodine, the resulting products have high purity and related impurities are undetectable.

The process is accomplished in a few easy and simple steps. The use of solid phase synthesis makes the process simpler and the use of Fmoc-chemistry eliminates the use of harsh chemicals like HF, thereby not affecting the product stability. The process eliminates purification of the intermediates, thereby increasing the yield and reducing the cost. Replacement of thiols as scavengers in step (b) and (e) makes the process more environment friendly and economical by not having to use scrubbers for thiols.

The choice of process often dictates the stability of the therapeutic peptide. There has been a long awaited requirement for obtaining peptide of formula (1), which will circumvent the limitations associated with the processes of prior art. Therefore, an industrial process of peptide synthesis containing tryptophan, disulfide loops, ε-NH$_2$ side chain, etc demands appropriate choice of protecting groups and reaction conditions to build up the peptide chain. This objective has been now successfully achieved by the Applicant developing a process described in entirety in the present application.

| Glossary of terms used herein | |
|---|---|
| AA | Amino acid |
| Acm | Acetamidomethyl |
| ACT | Activator |
| ADP | Adenosine diphosphate |
| AgOTf | Silver trifluoromethane sulfonate |
| Arg | Arginine |
| Asp | Aspartic acid |
| Boc/boc | tert-butyloxycarbonyl |
| Cys | Cysteine |
| DCM | Dichloromethane |
| Dde | 1-(4,4-dimethyl-2,6-dioxoyclohexylidene)ethyl |
| ivDde | 1-(4,4-dimethyl-2,6-dioxoyclohexylidene)-3-methyl butyl |
| DEP | Deprotection reagent |
| DMF | Dimethyl formamide |
| DMSO | Dimethyl sulphoxide |
| DTT | Dithiothreitol |
| EDT | Ethane dithiol |
| Fmoc | 9-fluorenylmethyloxycarbonyl |
| Glu | Glutamic acid |
| Gly | Glycine |
| HAR | Homoarginine |
| HBTU | 2-(1H-Benzotriazole-1-y1)-1,1,3,3-tetramethyluronium hexafluorophosphate |
| HF | Hydrogen fluoride |
| HIC | Hydrophobic Interaction Chromatography |
| His | Histidine |
| IEC | Ion Exchange Chromatography |
| LC-MS | Liquid Chromatography-Mass Spectroscopy |
| Lys | Lysine |
| Mmt | 4-methoxytrityl |
| Mpr | Mercaptopropionic Acid |
| Mtr | 4-methoxy-2,3,6-trimethylbenzenesulfonyl |
| Mtt | 4-methyltrityl |
| NMM | N-methyl morpholine |
| O-t-Bu | O-t-butyl |
| Pbf | 2,2,4,6,7-pentamethyldihydrobenzofuran-5-sulfonyl |
| Pmc | 2,2,5,7,8-pentamethylchroman-6-sulfonyl |

-continued

| Glossary of terms used herein | |
|---|---|
| PPP | Platelet poor plasma |
| Pro | Proline |
| PRP | Platelet rich plasma |
| RP-HPLC | Reverse Phase High Performance Liquid Chromatography. |
| RV | Reaction Vessel |
| Ser | Serine |
| SOLV | Solvent |
| SP | Synthetic Peptide |
| TEA | Triethylamine |
| TFA | Trifluoroacetic acid |
| Thr | Threonine |
| TIS | Triisopropylsilane |
| Trp | Tryptophan |
| Trt | Trityl |

SUMMARY

The present invention provides an improved process for the preparation of a peptide N$^6$-(aminoiminomethyl)-N$^2$-(3-mercapto-1-oxopropyl-L-lysylglycyl-L-α-aspartyl-L-tryptophyl-L-prolyl-L-cysteinamide, cyclic(1→6)-disulfide of formula (1)

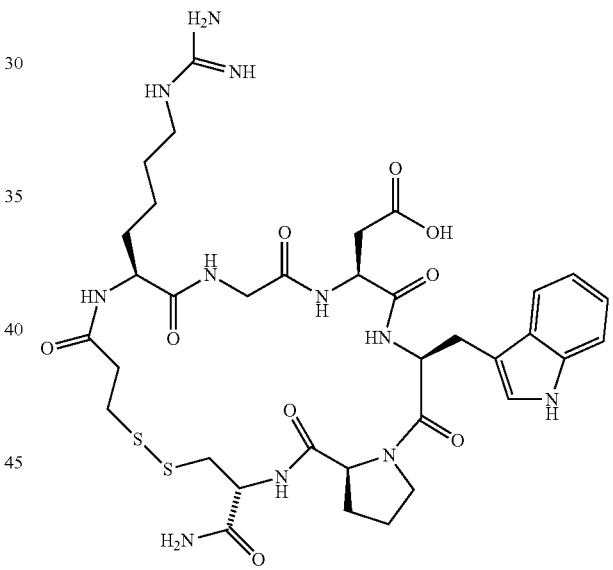

Formula (1)

on a solid support, comprising:
a. assembling a peptide chain comprising of six amino acids and a thioalkyl carboxylic acid in a required sequence on a solid support to obtain a peptide bound resin of formula (2) as given below:

(Trt)Mpr-Lys(Dde)-Gly-Asp(Otbu)-Trp-Pro-Cys(Trt)-solid support

Formula (2);

b. capping the free amino groups after each coupling of (a) with acetic anhydride;
c. cleaving Dde group in the peptide of formula (2) from the solid support to obtain peptide-solid support of formula (3)

(Trt)Mpr-Lys-Gly-Asp(Otbu)-Trp-Pro-Cys(Trt)-solid support

Formula (3);

d. guanylating the peptide of formula (3) at ϵ-lysine-$NH_2$ in an organic solvent to obtain peptide-solid support of formula (4) as given below:

(Trt)Mpr-Har-Gly-Asp(Otbu)-Trp-Pro-Cys(Trt)-solid support    Formula (4);

e. cleaving and deprotecting all groups in the peptide of step (d) from the solid support to obtain peptide-amide formula (5);

Mpr-Har-Gly-Asp-Trp-Pro-Cys-$CONH_2$
|                          |
S—H                    S—H;    Formula (5)

f. oxidizing the SH-peptide of formula (5) with an appropriate oxidizing agent to obtain the crude peptide-amide of formula (1); and g. purifying the crude peptide-amide of formula (1) by chromatographic technique.

In another aspect, the present invention relates to the solid support, wherein said support is either cellulose support or a resin support.

In yet another aspect, the present invention relates to the cellulose support, wherein said cellulose support is selected from a group consisting of cotton, gauze, fabric, paper and perloza beads.

The described process is simple, easy, environment friendly, takes lesser time and is more cost effective.

In one aspect, the present invention provides an intermediate peptide of formula (2)

(Trt)Mpr-Lys(Dde)-Gly-Asp(Otbu)-Trp-Pro-Cys(Trt)-Solid support    Formula (2)

In another aspect, the present invention provides an intermediate peptide of formula (3)

(Trt)Mpr-Lys-Gly-Asp(Otbu)-Trp-Pro-Cys(Trt)-Solid support    Formula (3);

In yet another aspect, the present invention provides an intermediate peptide of formula (4)

(Trt)Mpr-Har-Gly-Asp(Otbu)-Trp-Pro-Cys(Trt)-Solid support    Formula (4)

In still another aspect, the present invention provides an intermediate peptide salt of the formula (5)

Mpr-Har-Gly-Asp-Trp-Pro-Cys-$CONH_2$    Formula (5)
|                          |
S—H                    S—H

BRIEF DESCRIPTION OF FIGURES AND TABLE

FIG. 1: Analytical RP-HPLC elution profile of SH peptide (Column: PEP 100; C-18; 5μ; 150×3 mm; Flow rate: 0.5 ml/min; Injection vol: 20 μl; Solvent System: A: 0.1% TFA, B: 100% Acetonitrile).

Figure 2:
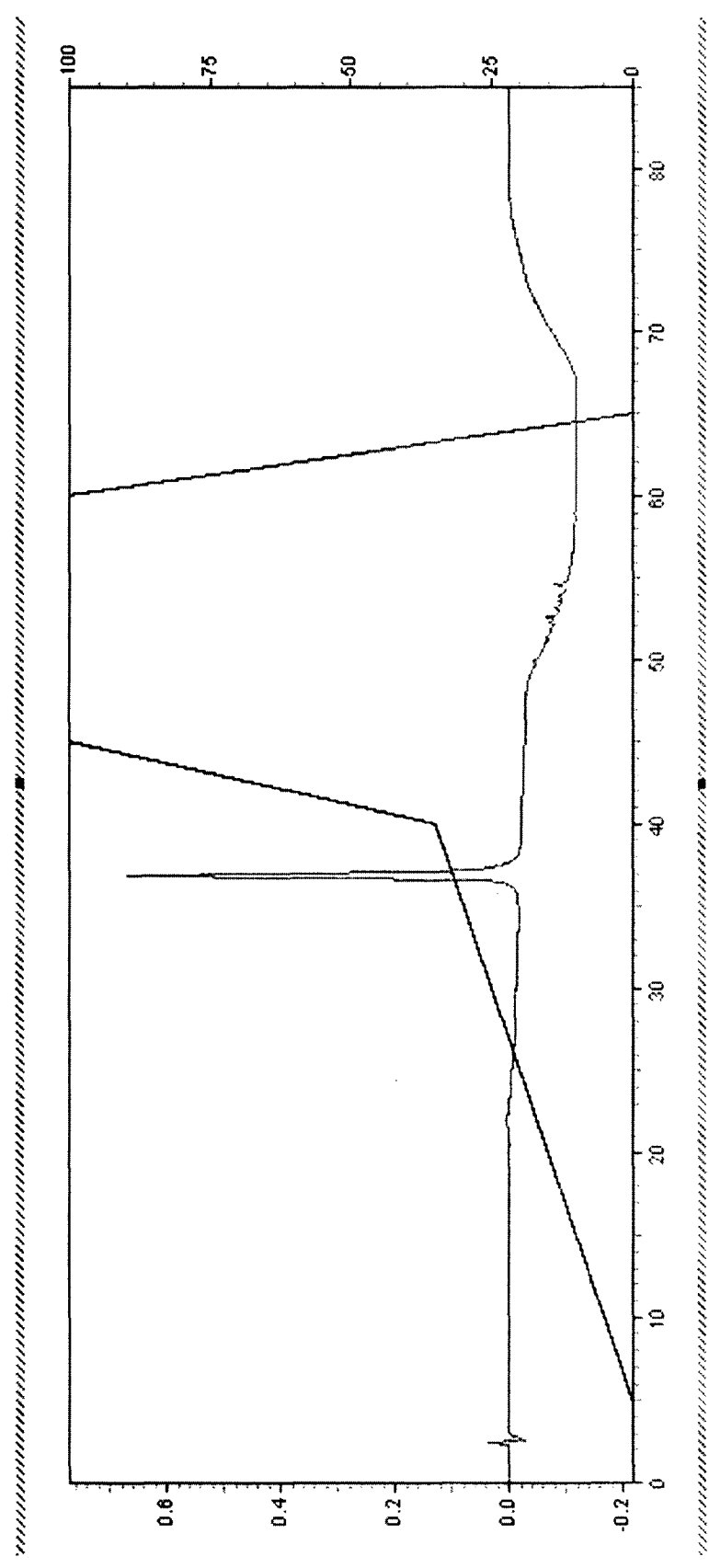

FIG. 2: Analytical RP-HPLC elution profile of purified cyclic peptide (Column: PEP 100; C-18; 5μ; 150×3 mm; Flow rate: 0.5 ml/min; Solvent System: A: 0.1% TFA, B: 100% Acetonitrile)

Figure 3:
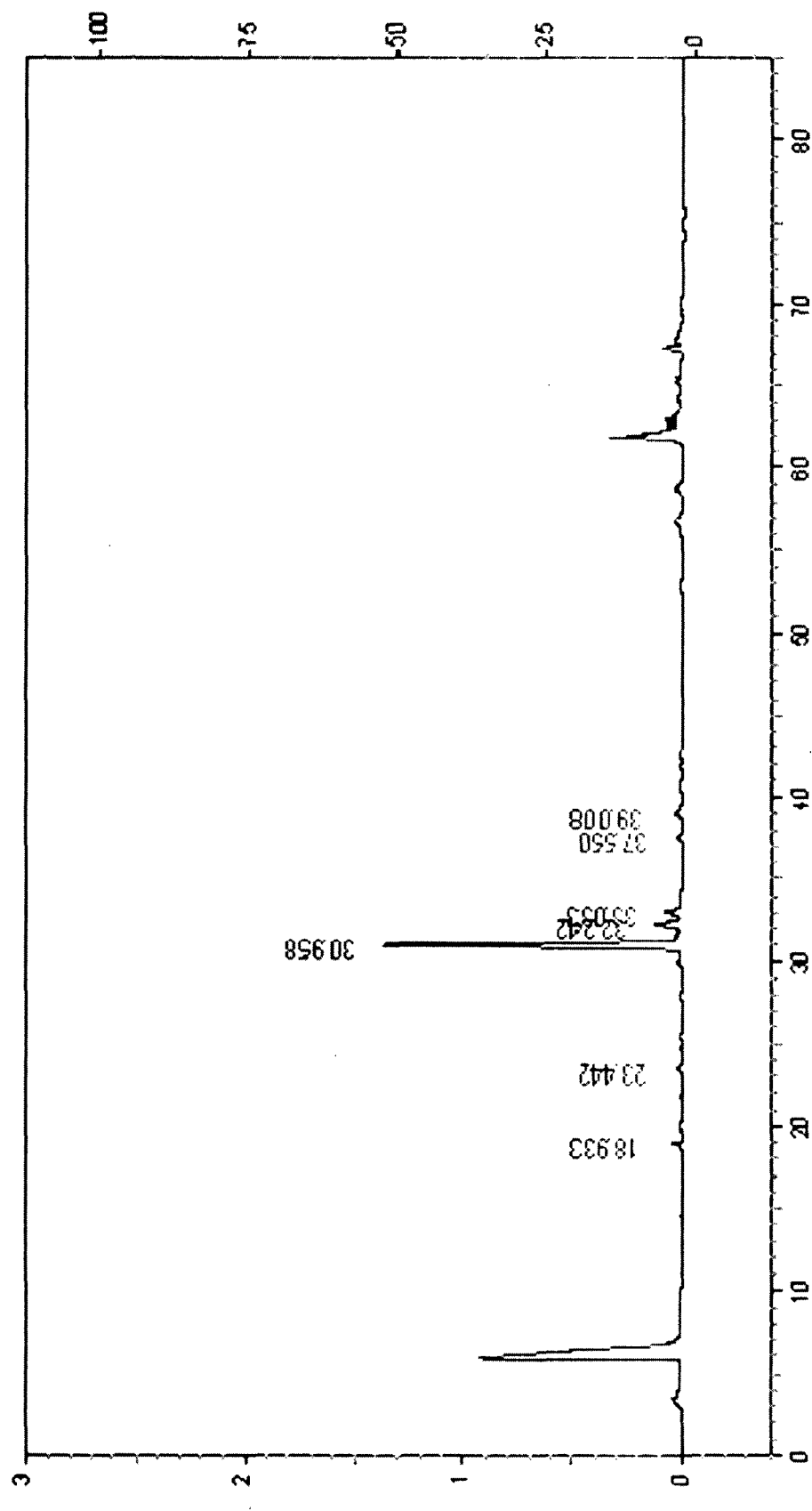

FIG. 3: Analytical RP-HPLC elution profile of HBTU—crude peptide from cellulose support (Column: PEP 300; C-18; 5μ; 150×3 mm; Flow rate: 0.5 ml/min; Injection vol: 20 μl; Solvent System: A: 0.1% TFA. B: 100% Acetonitrile).

Figure 4:
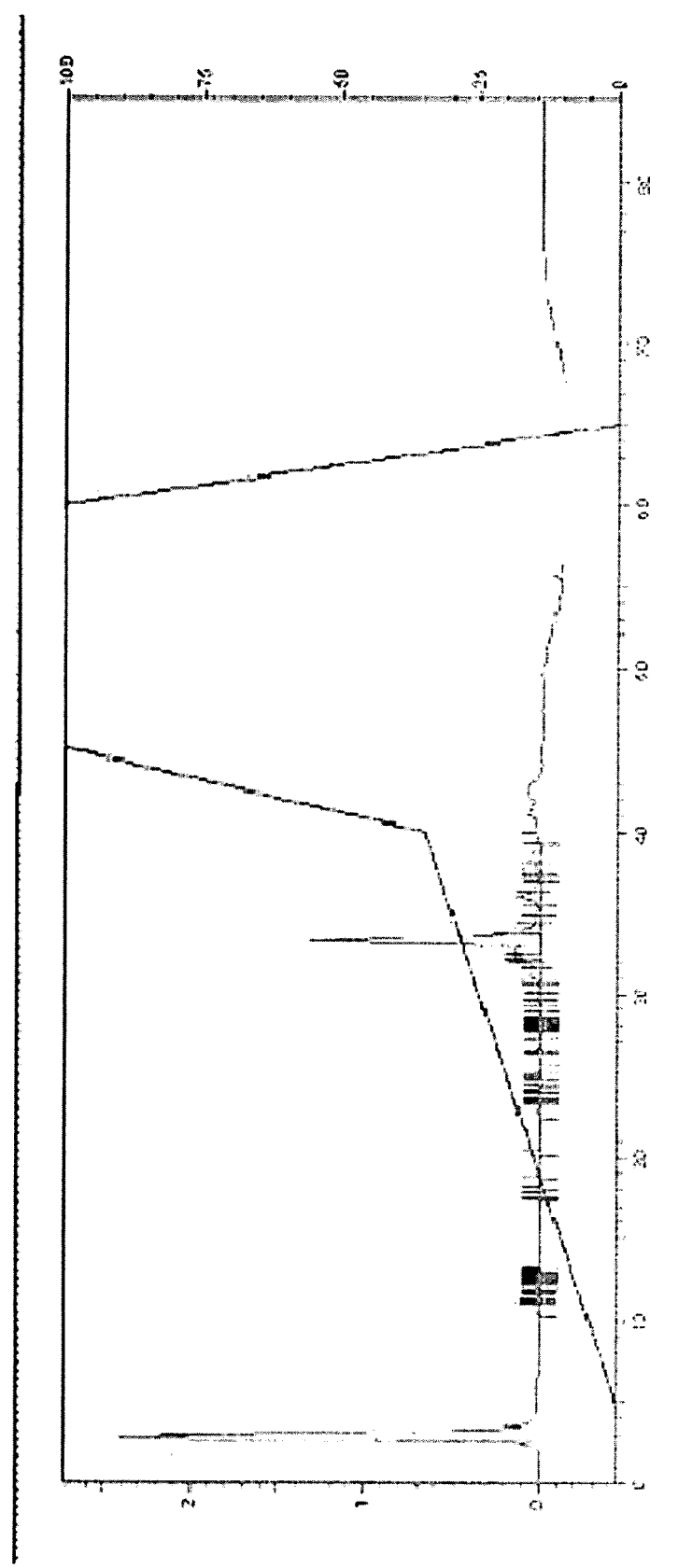

FIG. 4: Analytical RP-HPLC elution profile of crude guanylated peptide (Column: PEP 300; C-18; 5μ; 150×3 mm; Flow rate: 0.5 ml/min; Injection vol: 20 μl; Solvent System: A: 0.1% TFA, B: 100% Acetonitrile).

Figure 5:
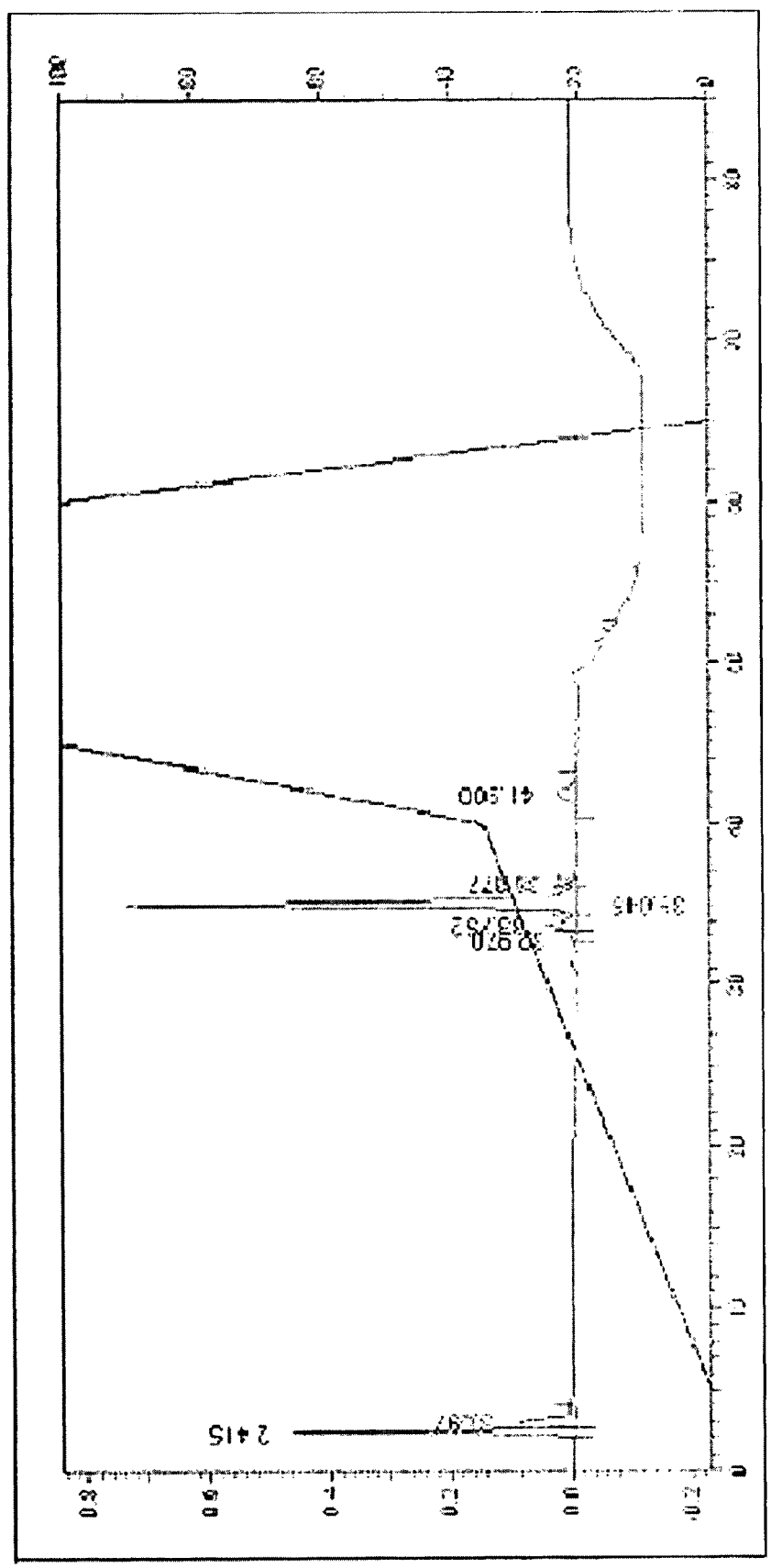

FIG. 5: Analytical RP-HPLC elution profile of crude cyclic peptide (Column: PEP 300; C-18; 5μ; 150×3 mm; Flow rate: 0.5 ml/min; Injection vol: 20 μl; Solvent System: A: 0.1% TFA, B: 100% Acetonitrile).

Figure 6:
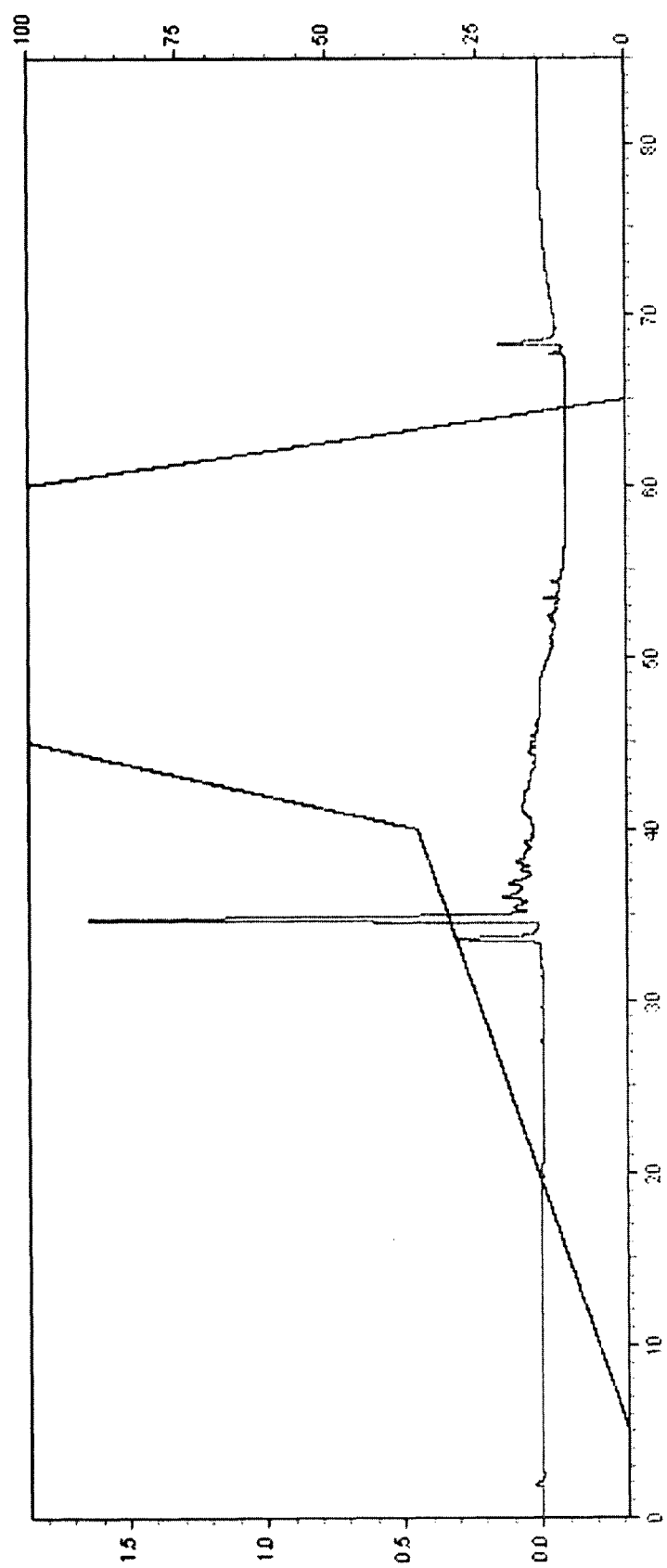

FIG. 6: Analytical RP-HPLC elution profile of purified cyclic peptide (Column: PEP 300; C-18; 5μ; 150×3 mm; Flow rate: 0.5 ml/min; Solvent System: A: 0.1% TFA, B: 100% Acetonitrile)

Figure 7:
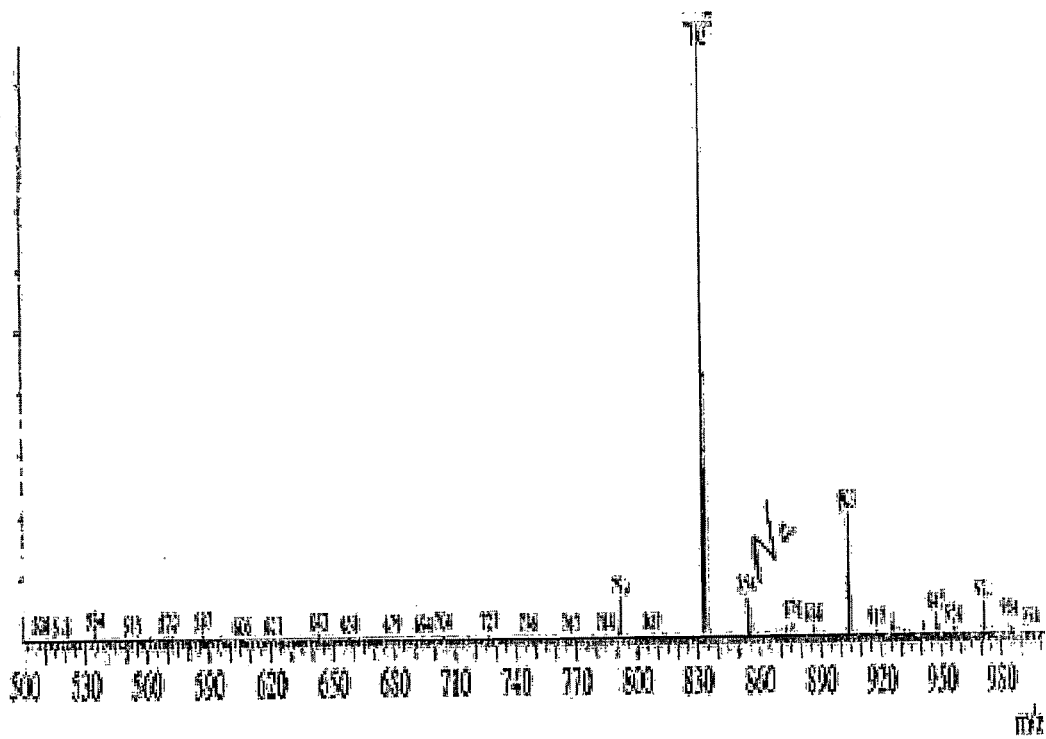

FIG. 7: MS Analysis of the pure peptide showing the mass to be 832.

DETAILED DESCRIPTION OF THE INVENTION

In accordance, the present invention provides an improved process for the preparation of a peptide $N^6$-(aminoiminomethyl)-$N^2$-(3-mercapto-1-oxopropyl-L-lysylglycyl-L-α-aspartyl-L-tryptophyl-L-prolyl-L-cysteinamide, cyclic(1→6)-disulfide of formula (1)

Formula (1)

on a solid support comprising:

a. assembling a peptide chain comprising of six amino acids and a thioalkyl carboxylic acid in a required sequence on a solid support to obtain a peptide bound resin of formula (2) as given below:

(Trt)Mpr-Lys(Dde)-Gly-Asp(Otbu)-Trp-Pro-Cys(Trt)-solid support    Formula (2);

b. capping the free amino groups after each coupling of (a) with acetic anhydride;

c. cleaving Dde group in the peptide of formula (2) from the solid support to obtain peptide-solid support of formula (3)

(Trt)Mpr-Lys-Gly-Asp(Otbu)-Trp-Pro-Cys(Trt)-solid support    Formula (3);

d. guanylating the peptide of formula (3) at F-lysine-NH₂ in an organic solvent to obtain peptide-solid support of formula (4) as given below:

(Trt)Mpr-Hat-Gly-Asp(Otbu)-Trp-Pro-Cys(Trt)-solid support

Formula (4);

e. cleaving and deprotecting all groups in the peptide of step (d) from the solid support to obtain peptide-amide formula (5);

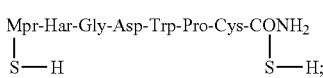

Formula (5)

f. oxidizing the SH-peptide of formula (5) with an appropriate oxidizing agent to obtain the crude peptide-amide of formula (1); and
g. purifying the crude peptide-amide of formula (1) by chromatographic technique.

In one embodiment, the present invention provides a process for the preparation of a peptide N⁶-(aminoiminomethyl)-N²-(3-mercapto-1-oxopropyl-L-lysylglycyl-L-α-aspartyl-L-tryptophyl-L-prolyl-L-cysteinamide, cyclic(1→6)-disulfide of formula (1), wherein the C-terminal of the protected first amino acid is bound to a solid support through a linker to obtain a solid support bound amino acid.

In another embodiment, the present invention provides a process for the preparation of a peptide of formula (1), wherein the solid support is derivatised with rink amide linker.

In yet another embodiment, the present invention provides a process for the preparation of a peptide of formula (1), wherein the solid support is either cellulose support or a rink amide resin support.

In still another embodiment, the present invention provides a process for the preparation of a peptide of formula (1), wherein the cellulose support is selected from a group consisting of cotton, gauze, fabric, paper and perloza beads.

One embodiment of the present invention provides a process for the preparation of a peptide of formula (1), wherein the amino acids used are selected from the group consisting of Cys, Pro, Trp, Asp, Gly, Lys, Arg, Har, Leu and Glu.

Another embodiment of the present invention provides a process for the preparation of a peptide of formula (1), wherein the thioalkyl carboxylic acid used is mercapto propionic acid (Mpr).

Yet another embodiment of the present invention provides a process for the preparation of a peptide of formula (1), wherein the organic solvent used for guanylation is selected from a group consisting of DMF, DCM, ethanol and methanol or mixture thereof.

Still another embodiment of the present invention provides a process for the preparation of a peptide of formula (1), wherein the guanylation is carried out using DMF.

Still yet another embodiment of the present invention provides a process for the preparation of a peptide of formula (1), wherein the peptide is cleaved from solid support using the reagents TFA, TIS, EDT, DCM, Phenol and water in a defined ratio, preferably TFA(85-98%): TIS(0-5%): H₂O(0-5%): EDT(0-5%): Phenol(0-5%), more preferably TFA(94.5-95.5%): TIS(0-2.5%): H₂O(0-3%): EDT(0-2.5%).

One embodiment of the present invention provides a process for the preparation of a peptide of formula (1), wherein the precipitation is carried out by using a solvent selected from the group consisting of acetone, acetonitrile, methanol, ethers, pentane and hexane or mixture thereof.

Yet another embodiment of the present invention provides a process for the preparation of a peptide of formula (1), wherein the precipitation is carried out using diisopropyl ether.

Still another embodiment of the present invention provides a process for the preparation of a peptide of formula (1), wherein the peptide of formula (1) obtained has purity more than 99%.

Still yet another embodiment of the present invention provides a process for the preparation of a peptide of formula (1), wherein the peptide of formula (1) obtained is further converted into its acetate salt by ion-exchange chromatography.

One embodiment of the present invention provides an intermediate peptide of formula (2):

(Trt)Mpr-Lys(Dde)-Gly-Asp(Otbu)-Trp-Pro-Cys(Trt)-Solid support

Formula (2)

Another embodiment of the present invention provides an intermediate peptide of formula (3)

(Trt)Mpr-Lys-Gly-Asp(Otbu)-Trp-Pro-Cys(Trt)-Solid support

Formula (3);

Yet another embodiment of the present invention provides an intermediate peptide of formula (4):

(Trt)Mpr-Har-Gly-Asp(Otbu)-Trp-Pro-Cys(Trt)-Solid support

Formula (4)

Still another embodiment of the present invention provides an intermediate peptide salt of the formula (5)

Formula (5)

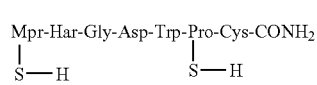

Another embodiment of the present invention relates to the use of a linker with the solid support preferably a rink amide linker.

Yet another embodiment of the present invention relates to the use of cellulose as solid support, preferably cotton.

Still another embodiment of the present invention relates to the use of first protected amino acid as Fmoc protected cysteine.

Yet another embodiment of the present invention relates to the use of HBTU as the coupling agent.

Still yet another embodiment of the present invention provides a cleavage of the cellulose support with the linker leading to release of peptide amide.

Yet another embodiment of the present invention provides peptide amide compound of formula (1) obtained by linking each of terminal functionality, which is an amino or carboxylic acid group or derivatives thereof.

Still another embodiment of the present invention relates to the use of amino acids selected from the group consisting of Cys, Pro, Trp, Asp, Lys, Gly, Arg, Har, Leu and Glu.

An embodiment of the present invention relates to the use of a thioalkyl carboxylic acid preferably mercapto propionic acid (Mpr).

Another embodiment of the present invention relates to the use of protecting groups for amino function of an amino acid as Fmoc or Boc.

Yet another embodiment of the present invention relates to the use of carboxyl function as unprotected or protected OtBu ester.

Still another embodiment of the present invention relates to the use of Trt group as a protecting group for thiol-function.

Still yet another embodiment of the present invention provides cleavage of the peptide from cellulose support using the reagents TFA, TIS, EDT, DCM, phenol and water in a defined ratio, preferably TFA(85-98%): TIS(0-5%): H$_2$O(0-5%): EDT(0-5%): Phenol(0-5%), more preferably TFA(94.5-95.5%): TIS(0-2.5%): H$_2$O(0-3%): EDT(0-2.5%).

Another embodiment of the present invention relates to the use of an organic solvent for guanylation selected from a group consisting of DMF, ethanol and methanol.

Yet another embodiment of the present invention provides the guanylation of peptide preferably by using the solvent DMF.

Yet another embodiment of the present invention relates to cleavage and de-protection of all groups in the peptide-amide of formula (4) from the solid support to obtain peptide-amide of formula (5).

Still another embodiment of the present invention provides the precipitation of the peptide amide of formula (5) using a solvent selected from the group consisting of acetone, acetonitrile, methanol, ethers, pentane, hexane and a mixture thereof.

Still yet another embodiment of the present invention provides the precipitation of the peptide amide of formula (5) by using Diisopropyl ether (DIPE).

Another embodiment of the present invention relates to the purification of the peptide of formula (5) by RP-HPLC.

Still yet another embodiment of the present invention provides the oxidation of SH-peptide of formula (5) with an appropriate oxidizing agent to obtain crude peptide-amide formula (1).

Still yet another embodiment of the present invention provides the purification of crude peptide-amide formula (1) by chromatographic techniques.

Yet another embodiment of the present invention relates to the peptide amide of formula (1) obtained having purity more than 99%.

Another embodiment of the present invention provides the acetate salt of formula (1) from peptide amide of formula (1).

Yet another embodiment of the present invention relates to the preparation of the peptide of formula (1) by solid phase synthesis using Fmoc chemistry.

Still another embodiment of the present invention uses methanol for purification of crude peptide enabling the process inexpensive.

Yet another embodiment of the present invention provides process for preparation of an intermediate peptide of formula (2) as given under:

(Trt)Mpr-Lys(Dde)-Gly-Asp(OtBu)-Trp-Pro-Cys(Trt)-Solid support   Formula (2)

Still another embodiment of the present invention provides process for preparation of an intermediate peptide amide of formula (3) as given under:

(Trt)Mpr-Lys-Gly-Asp(OtBu)-Trp-Pro-Cys(Trt)-Solid support   Formula (3)

Still yet another embodiment of the present invention provides process for preparation of a peptide amide of formula (4) as given below:

(Trt)Mpr-Homoarg-Gly-Asp(OtBu)-Trp-Pro-Cys(Trt)-Solid support   Formula (4)

Yet another embodiment of the present invention provides a process for preparation of an intermediate —SH peptide amide of formula (5) as given under:

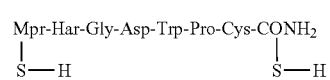

Formula (5)

The present invention also provides a process for the preparation of a peptide N6-(aminoiminomethyl)-N2-(3-mercapto-1-oxopropyl)-L-lysylglycyl-L-α-aspartyl-L-tryptophyl-L-prolyl-L-cysteinamide, cyclic(1→6)-disulfide of formula (1) on a cellulose support, said process comprising:

a. assembling a peptide chain comprising of six amino acids and a thioalkyl carboxylic acid in a required sequence on a solid cellulose support by coupling, to directly join one another by peptide bonds to obtain peptide of formula (6);

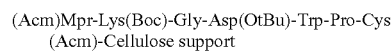

Formula (6)

b. capping the free amino groups of step (a) after each coupling with acetic anhydride;
c. cleaving and deprotecting all groups except Acm group in the peptide of step (b) from the cellulose Support to obtain peptide-amide of formula (7)

Formula (7);

d. guanylating the peptide of step (c) at ε-lysine-NH2 in an organic solvent followed by precipitating with another solvent to obtain peptide-amide of formula (8)

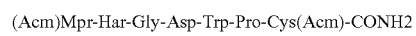

Formula (8)

e. treating the peptide amide of Formula (8) of step(d) with a heavy metal salt in an appropriate solvent, followed by precipitating using an organic solvent to obtain the heavy metal-peptide salt of formula (9)

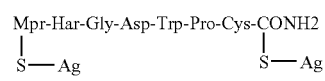

Formula (9)

f. treating the heavy metal-peptide salt of step (e) with an appropriate nucleophilic reagent to obtain the crude peptide amide of formula (1); and
g. purifying the crude peptide amide of step (f) by chromatographic techniques.

An embodiment of the present invention involves reaction of amino and carboxylic equivalent of compounds to form said peptide bond.

Another embodiment of the present invention provides C-terminal of the protected first amino acid bound to a cellulose support through a linker to obtain a solid phase bound amino acid.

Yet another embodiment of the present invention uses cellulose as solid support, preferably cotton, gauze fabric, paper or perloza bead.

Still another embodiment of the present invention uses first protected amino acid as thiol protected Fmoc cysteine.

Yet another embodiment of the present invention uses HBTU as the coupling agent.

Still yet another embodiment of the present invention provides a cleavage of the cellulose support with the linker leading to release of assembled peptide amide.

Yet another embodiment of the present invention provides peptide amide compound of formula (1) obtained by linking each of terminal functionality, which is an amino or carboxylic acid group or derivatives thereof.

Still another embodiment of the present invention uses amino acids selected from the group consisting of Cys, Pro, Trp, Asp, Lys, Gly, Arg, Har, Leu and Glu.

An embodiment of the present invention uses thioalkyl carboxylic acid, mercapto propionic acid Another embodiment of the present invention utilizes an organic solvent for guanylation selected from a group consisting of DMF, ethanol and methanol.

In yet another embodiment of the present invention, the guanylation of peptide is performed preferably by using the solvent DMF.

In still another embodiment of the present invention, the precipitation of the peptide of formula (8) is performed using a solvent selected from the group consisting of acetone, acetonitrile, methanol, ethers, pentane, hexane and a mixture thereof.

In still yet another embodiment of the present invention, the precipitation is performed using acetonitrile.

Another embodiment of the present invention provides the purification of the peptide of formula (8) using RP-HPLC.

Another embodiment provides for the preparation of the acetate salt of formula (1) from peptide amide of formula (1).

Yet another embodiment of the present invention provides the process for preparation of the peptide of formula (1) by solid phase synthesis using Fmoc chemistry.

Another embodiment of the present invention provides heavy metal salts for removal of Acm selected from thallium trifluoromethane sulphonate, mercuric acetate or silver trifluoromethane sulphonate.

In another embodiment of the present invention, the heavy metal peptide salt is obtained by preferably treating peptide of formula (8) with silver trifluoromethane sulphonate in TFA.

Yet another embodiment of the present invention is that the precipitation of the heavy metal-peptide salt of Formula (9) is preferably carried out using an ethereal solvent and more preferably diisopropyl ether.

Still another embodiment of the present invention is that the heavy metal-peptide salt may be treated with HCl and DMSO to simultaneously remove the heavy metal and to oxidize the resulting peptide to yield crude peptide amide of formula (1).

Still yet another embodiment of the present invention is that the crude peptide amide of formula (1) can be purified by RP-HPLC.

Another embodiment of the present invention the purification of crude peptide amide of formula (1) is preferentially performed by RP-HPLC using C-4, C-8 or C-18 silica or polymer reverse phase columns using methanol and/or acetonitrile in combination with aqueous TFA (0-0.5%) as mobile phase.

Still another embodiment of the present invention uses methanol (AR grade) for purification of crude peptide enabling the process inexpensive.

Yet another embodiment of the present invention provides a process for preparation of an intermediate peptide of formula (6)

(Acm)Mpr-Lys(Boc)-Gly-Asp(OtBu)-Trp-Pro-Cys
(Acm)-Cellulose support  Formula (6)

Still another embodiment of the present invention provides process for preparation of an intermediate peptide amide of formula (7)

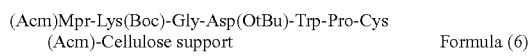

(Acm)Mpr-Lys-Gly-Asp-Trp-Pro-Cys(Acm)-CONH$_2$  Formula (7)

Still yet another embodiment of the present invention provides process for preparation of a peptide amide of formula (8)

(Acm)Mpr-Har-Gly-Asp-Trp-Pro-Cys(Acm)-CONH$_2$  Formula (8)

Yet another embodiment of the present invention provides process for preparation of an intermediate peptide amide silver salt of formula (9)

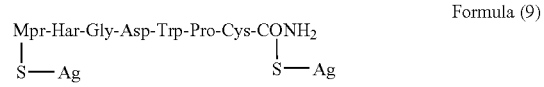

Another embodiment describes the process for chemical synthesis of linear peptide of formula 2, for detailed description see Example 1.

Yet another embodiment describes the process for the removal of Dde group from the assembled peptide resin, for detailed description see Example 2.

Still another embodiment describes the process for the guanylation of Peptide-Resin to yield peptide of formula 4, for detailed description see Example 3.

Still yet another embodiment describes the process for the cleavage of the Peptide from the Resin to yield Peptide Amide to yield peptide of formula 5, for details see example 4.

Another embodiment describes the process of oxidation of the linear peptide to yield formula 1, for details see example 5.

Yet another embodiment describes the process of purification of the peptide, for details see example 6 and 7

Still yet another embodiment describes the process of Chemical synthesis of linear peptide using a Cellulose Support, for details see example 8.

Another embodiment describes the process of cleavage of the peptide from the cellulose support to yield peptide amide of formula 7, for details see example 9.

Yet another embodiment describes the process of Guanylation of Crude Peptide to yield peptide amide of formula 8, for details see example 10.

Still yet another embodiment describes the process of DE-ACM of the Guanylated Peptide Followed by Oxidation to Yield peptide of formula 1, for details see example 11.

Another embodiment describes the process of purification of S—S Peptide of formula 1, for details see example 12 and 13.

Yet another embodiment describes the process of preparation of acetate salt of Formula (1), for details see example 14.

The following examples are put forth so as to provide those of ordinary skill in the art with a complete disclosure and the description of how to make and use the present invention, and are not intended to limit the scope of what the inventors regard as their invention nor are they intended to represent that the experiments below are all and only experiments performed.

EXAMPLES

Example (1)

Chemical Synthesis of Linear Peptide

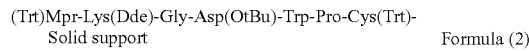

The assembly of the peptide chain is carried out in the following manner. The solid support is transferred to the RV of the peptide synthesizer [CS936, CS BIO, Calif. Peptide Synthesizer] and the lineal peptide is assembled on it using 1.5-4.0 times molar excess amino acid derivatives, on the peptide synthesizer. The solid support could be a resin or a cellulose support such as fabric. The first amino acid, Fmoc-Cys (C), is coupled to the solid support by deprotecting the Fmoc-group on the solid support, followed by activating the Fmoc-Cys(C) by HBTU in the presence of NMM. For coupling of the next amino acid, Proline, the α-nitrogen of the first amino acid i.e. Fmoc-Cys(C), is deprotected followed by activating the Fmoc-Pro by HBTU in the presence of NMM. This process is repeated with all the amino acids till the entire linear peptide chain is assembled on the solid support. The Mpr is assembled at the end. Each coupling is carried out for a time range of 45-90 min. The coupling steps are followed by capping with acetic anhydride for 30-60 min. After the couplings are complete, the solid support is washed with organic solvent/s which may be selected from the range of DMF, N-methyl pyrrolidone or DCM, preferably DMF followed by DCM, and then dried under vacuum. The linear peptide of formula (2) is obtained.

The peptide was synthesized as peptide amide by solid phase peptide synthesis technology on solid Support using Fmoc chemistry.

| Solid support | Rink amide resin or a cellulose support (0.65 mm/g) |
| --- | --- |
| Activator | HBTU/0.4M NMM |
| Solvent | Dimethyl Formamide |
| Deprotection | 20% Piperidine |

The peptide was synthesized as peptide amide by solid phase peptide synthesis technology on a rink amide resin using Fmoc chemistry; cellulose supports like fabric can also be used for the peptide synthesis. The resin (15.38 g-rink amide, 10 mmole) was transferred to the RV of the CS936 and swollen in DMF.

(i) Synthesis of Fmoc Cys(Trt)-resin by coupling of Fmoc-Cys(Trt)/HBTU to the resin. The pre-swollen resin (10 mmole) was washed twice with DMF followed by removal of Fmoc by treatment with 20% piperidine twice. The resin was washed 6 times with DMF. Fmoc Cys(Trt)(20 mmoles) and HBTU (equimole to amino acid) were dissolved in 0.4M NMM and added to the resin. Coupling was carried out for 60 min under optimized stirring. The resin was washed once again with DMF thrice. After the coupling, the free amino groups were capped by acetic anhydride (2.5M) for 45 min followed by washing with DMF three times. This HBTU process is a one-step process wherein ester is not isolated.

The synthesis cycle was programmed as follows:

| Step | Reagent | Time | Repeat | Activity |
| --- | --- | --- | --- | --- |
| 1 | SOLV | 10 min | X3 | WASHES RESIN |
| 2 | DEP | 5 min | X2 | DEP N-TERMINUS |
| 3 | SOLV | 30 sec | X6 | WASHES RESIN |
| 4 | ACT | 30 sec | X1 | DISSOLVES Fmoc-Cys (Trt)/HBTU |
| 5 | AA | 45 min | X1 | Fmoc-Cys (Trt) COUPLING |
| 6 | SOLV | 30 sec | X3 | WASHES RESIN |

(ii) Synthesis of Fmoc-Pro-Cys(Trt)-resin by coupling Fmoc-Pro/HBTU to Fmoc-Cys(Trt)-resin. The reaction was carried out as in step 1. The synthesis cycle was programmed as follows:

| Step | Reagent | Time | Repeat | Activity |
| --- | --- | --- | --- | --- |
| 1 | SOLV | 30 sec | X3 | WASHES RESIN |
| 2 | DEP | 5 min | X2 | DEP N-TERMINUS |
| 3 | SOLV | 30 sec | X6 | WASHES RESIN |
| 4 | ACT | 30 sec | X1 | DISSOLVES Fmoc-Pro/HBTU |
| 5 | AA | 45 min | X1 | COUPLING Fmoc-Pro |
| 6 | SOLV | 30 sec | X3 | WASHES RESIN |

(iii) Synthesis of Fmoc-Trp-Pro-Cys(Trt)-resin by coupling Fmoc-Trp/HBTU to Fmoc-Pro-Cys(Trt)-resin. The reaction was carried out as in step 1. The synthesis cycle was programmed as follows:

| Step | Reagent | Time | Repeat | Activity |
| --- | --- | --- | --- | --- |
| 1 | SOLV | 30 sec | X3 | WASHES RESIN |
| 2 | DEP | 5 min | X2 | DEP N-TERMINUS |
| 3 | SOLV | 30 sec | X6 | WASHES RESIN |
| 4 | ACT | 30 sec | X1 | DISSOLVES Fmoc-Trp/HBTU |
| 5 | AA | 45 min | X1 | COUPLING Fmoc-Trp |
| 6 | SOLV | 30 sec | X3 | WASHES RESIN |

(iv) Synthesis of Fmoc-Asp(OtBu)-Trp-Pro-Cys(Trt)-resin by coupling Fmoc-Asp (O-t-Bu)/HBTU to Fmoc-Trp-Pro-Cys(Trt)-resin. The reaction was carried out as in step 1. The synthesis cycle was programmed as follows:

| Step | Reagent | Time | Repeat | Activity |
| --- | --- | --- | --- | --- |
| 1 | SOLV | 30 sec | X3 | WASHES RESIN |
| 2 | DEP | 5 min | X2 | DEP N-TERMINUS |
| 3 | SOLV | 30 sec | X6 | WASHES RESIN |
| 4 | ACT | 30 sec | X1 | DISSOLVES Fmoc-Asp(OtBu)/HBTU |
| 5 | AA | 45 min | X1 | COUPLING Fmoc-Asp(OtBu) |
| 6 | SOLV | 30 sec | X3 | WASHES RESIN |

(v) Synthesis of Fmoc-Gly-Asp (OtBu)-Trp-Pro-Cys(Trt)-resin by coupling Fmoc-Gly/HBTU to Fmoc-Asp(O-t-Bu)-Trp-Pro-Cys(Trt)-resin. The reaction was carried out as in step 1. The synthesis cycle was programmed as follows:

| Step | Reagent | Time | Repeat | Activity |
| --- | --- | --- | --- | --- |
| 1 | SOLV | 30 sec | X3 | WASHES RESIN |
| 2 | DEP | 5 min | X2 | DEP N-TERMINUS |
| 3 | SOLV | 30 sec | X6 | WASHES RESIN |
| 4 | ACT | 30 sec | X1 | DISSOLVES Fmoc-Gly/HBTU |
| 5 | AA | 45 min | X1 | COUPLING Fmoc-Gly |
| 6 | SOLV | 30 sec | X3 | WASHES RESIN |

(vi) Synthesis of Fmoc-Lys(Dde)-Gly-Asp(OtBu)-Trp-Pro-Cys(Trt)-resin by coupling Fmoc-Lys(Dde)/HBTU to Fmoc-Gly-Asp(OtBu)-Trp-Pro-Cys(Trt)-resin. The reaction was carried out as in step 1. The synthesis cycle was programmed as follows:

| Step | Reagent | Time | Repeat | Activity |
|---|---|---|---|---|
| 1 | SOLV | 30 sec | X3 | WASHES RESIN |
| 2 | DEP | 5 min | X2 | DEP N-TERMINUS |
| 3 | SOLV | 30 sec | X6 | WASHES RESIN |
| 4 | ACT | 30 sec | X1 | DISSOLVES Fmoc-Lys(Dde)/HBTU |
| 5 | AA | 45 min | X1 | COUPLING Fmoc-Lys(Dde) |
| 6 | SOLV | 30 sec | X3 | WASHES RESIN |

(vii) Synthesis of Mpr(T-t)-Lys(Dde)-Gly-Asp(OtBu)-Trp-Pro-Cys(Trt)-resin by coupling Mpr(Trt)/HBTU to Fmoc-Lys(Dde)-Gly-Asp(OtBu)-Trp-Pro-Cys(Trt)-resin. The reaction was carried out as in step 1. The synthesis cycle was programmed as follows:

| Step | Reagent | Time | Repeat | Activity |
|---|---|---|---|---|
| 1 | SOLV | 30 sec | X3 | WASHES RESIN |
| 2 | DEP | 5 min | X2 | DEP N-TERMINUS |
| 3 | SOLV | 30 sec | X6 | WASHES RESIN |
| 4 | ACT | 30 sec | X1 | DISSOLVES Mpr(Trt)/HBTU |
| 5 | AA | 45 min | X1 | COUPLING Mpr(Trt) |
| 6 | SOLV | 30 sec | X3 | WASHES RESIN |

In the synthesis coupling of Mpr(Trt) had to be carried out twice to complete the coupling reaction.

Example (2)

Removal of Dde Group from the Assembled Peptide Resin (Trt)-Mpr-Lys-Gly-Asp(OtBu)-Trp-Pro-Cys(Trt)-Solid support Formula 3

The assembled peptidyl resin (1.3 g) is swelled with 25 ml of DMF for an hour and filtered through RV. The peptide-resin is then treated with freshly prepared 25 ml of 2% Hydrazine hydrate in DMF for 5 mins followed by filtration under vacuum. The peptide-resin is subjected to 25 ml of 2% Hydrazine hydrate in DMF again for another 7 min and filtered by vacuum. The resin is washed with DMF.

Example (3)

Guanylation of Peptide-Resin to Yield (Trt)-Mpr-Har-Gly-Asp(OtBu)-Trp-Pro-Cys(Trt)-Solid support Formula 4

The Dde deprotected resin is suspended in 6 ml of DMF, the pH adjusted to 9 with TEA. The reagent 3,5 dimethyl pyrazole-1-carboxamidine nitrate (160.6 mg) in DMF(1.98 ml) is added to the peptide-resin of formula (3). The reaction mixture is stirred at 30° C. for 4 days with multiple additions of one time excess of reagent 3,5-dimethylpyrazole-1-carboxamidine nitrate.

The peptide resin of formula (4) is filtered and washed with DMF followed by MeOH wash. The peptide-resin is dried for 18 hrs under vacuum.

Example (4)

Cleavage of the Peptide from the Resin to Yield Peptide Amide

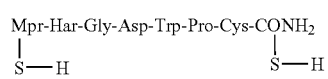

Formula 5

The guanylated peptide resin (from Example 3) is treated with 500 ml of cleavage cocktail consisting of TFA (95%): TIS(2.5%): $H_2O$(2.5%): EDT(0%): Phenol (0%) for 2 hrs at R.T in CS936. The reaction mixture is filtered through RV, and TFA was evaporated on Rotavap. Precipitation of the peptide was carried out at −20° C. by addition of 300 ml of cold diisopropyl ether with constant stirring. The crude peptide precipitate in the solvent is let to stand at −20° C. for 10 hrs. The peptide was isolated by filtering through Whatman paper no. 5, followed by cold solvent wash (100 ml×3) to remove the scavengers used in the cleavage cocktail. The crude peptide precipitate is dried under vacuum over $P_2O_5$, and characterized by RP-HPLC (FIG. 1).

The Percentage Purity of the peptide obtained is 90% having a yield of 68%.

Example (5)

Oxidation of the Linear Peptide to Yield

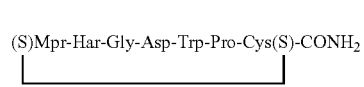

(Formula 1)

The oxidation of linear peptide is carried out by dissolving 10 mg of the peptide in 20 ml of 20% DMSO in 10% acetic acid at RT. The reaction mixture is stirred for 7 hrs at 25° C. The reaction mixture is checked for completion of oxidation. On completion of the reaction crude peptide of formula (1) is obtained. The Percentage Purity of the peptide obtained is 85%.

Example (6)

Purification of S—S Peptide

The crude disulfide looped peptide of formula (1) is loaded on to prep C-18 column (50×250 mm, 100 Å). The peptide is purified by using aqueous TFA (0.1%) and methanol in a gradient program. This is followed by an isocratic run using the above said solvent systems on a Shimadzu preparative HPLC System consisting of a controller, 2 LC8A pumps, and UV-Vis detector. The purified peptide amide of formula (1) is analysed by analytical RP-HPLC (FIG. 2). The mass is determined by Mass Spectrophotometer.

Example (7)

Purification of S—S Peptide

The purification was carried out in the same manner as carried out in Example 6, except that acetonitrile was used instead of methanol to obtain peptide amide of formula (1).

Example (8)

Chemical Synthesis of Linear Peptide Using a Cellulose Support (Acm)Mpr-Lys(Boc)-Gly-Asp(OtBu)-Trp-Pro-Cys
(Acm)-cellulose support                              Formula (6)

The assembly of the peptide is carried out in the following manner. The Rink amide cellulose was transferred to an adjustable bed chromatography column attached with a PTFE plunger. The Rink amide cellulose bundles were stacked one on top of the other in the glass column, the height of the bed was adjusted by screwing the column end piece down until it was fitted just above the cellulose support. The solvents and the reagents were superfluously flushed in the column using a HPLC pump LC-2010. The linear peptide is assembled on to the cellulose support using 1.5-4.5 equivalents mole excess amino acid derivative. The first amino acid derivative Fmoc-Cys (Acm)-OH is coupled to the cellulose by deprotecting the Fmoc group on the cellulose, followed by activation of the Fmoc-Cys (Acm)-OH using HBTU as the coupling reagent in presence of NMM. For the second amino acid coupling, Fmoc (Pro)-OH, the Fmoc group of the first amino acid, Cys(Acm)-OH is deprotected followed by activating the Fmoc-Pro-OH by HBTU in presence if NMM. The cycle is repeated by coupling the appropriate amino acids until the desired sequence is assembled on the cellulose support. Each coupling is performed for 45-90 minutes. The deprotection of the Fmoc groups is performed using a solution of 20% piperidine in DMF for 10 minutes. After the coupling steps are complete, the peptidyl cellulose is washed with organic solvent/s like DMF, DCM and then dried under vacuum. The linear peptide of formula (6) is obtained.

The peptide was synthesized as a peptide amide by the solid phase peptide synthesis technology on rink amide cellulose using continuous or batch wise additions using a Shimadzu LC pump 2010. The synthesis was performed using Fmoc chemistry.

| | |
|---|---|
| Instrument | LC 2010 pump |
| Solid support | Rink amide cellulose support (0.5 mmol/g) |
| Activator | HBTU/0.4M NMM |
| Solvent | Dimethyl Formamide |
| Deprotection | 20% Piperidine |

The Rink amide cellulose support (20 g, 10 mmol) was transferred to the adjustable bed chromatography column attached with a PTFE plunger, which was attached to HPLC pump. Connections with the pump were made using PTFE tubings and stainless steel valves. The valve arrangements were imparted such that the solvents/reagents could be recycled or could be connected to the waste from the column.

(i) Synthesis of the Fmoc Cys(Acm)-Cellulose by Coupling of the Fmoc-Cys(Acm)/HBTU to the Cellulose.

The Rink amide cellulose support (10 mmol) was washed with DMF followed by removal of Fmoc by treatment with 20% piperidine. The Rink amide cellulose support was then washed with DMF. Fmoc Cys (Acm) (25 mmoles) and HBTU (equimole to amino acid) were dissolved in 0.4 M NMM and added to the Rink amide cellulose support. Coupling was carried out by recycling the cocktail mixture for 60 minutes. The coupling step is executed by generating the activated HBTU complex insitu. The peptidyl cellulose support was then washed with DMF thoroughly.

The synthesis cycle was programmed as follows:

| Step | Reagent | Time | Repeat | Volume | Activity |
|---|---|---|---|---|---|
| 1 | SOLV | 10 | X3 | 100 ml | WASHES SUPPORT |
| 2 | DEP | 10 min | X2 | 100 ml | DEP N-TERMINUS |
| 3 | SOLV | — | X6 | 100 ml | WASHES SUPPORT |
| 4 | ACT | 30 sec | X1 | 60 ml | DISSOLVES Fmoc-Cys (Acm) |
| 5 | AA | 60 min | X1 | — | Fmoc-Cys (Acm) COUPLING |
| 6 | SOLV | — | X3 | 100 ml | WASHES SUPPORT |

(ii) Synthesis of the Fmoc-Pro-Cys(Acm)-Cellulose by Coupling of the Fmoc-Pro/HBTU to the Fmoc Cys(Acm)-Cellulose.

The reaction was carried out as in step i. The synthesis cycle was programmed as follows.

| Step | Reagent | Time | Repeat | Volume | Activity |
|---|---|---|---|---|---|
| 1 | SOLV | 10 | X3 | 100 ml | WASHES SUPPORT |
| 2 | DEP | 10 min | X2 | 100 ml | DEP N-TERMINUS |
| 3 | SOLV | — | X6 | 100 ml | WASHES SUPPORT |
| 4 | ACT | 30 sec | X1 | 60 ml | DISSOLVES Fmoc-Pro |
| 5 | AA | 60 min | X1 | — | Fmoc-Pro COUPLING |
| 6 | SOLV | — | X3 | 100 ml | WASHES SUPPORT |

(iii) Synthesis of the Fmoc-Trp-Pro-Cys(Acm)-Cellulose by Coupling of the Fmoc-Trp/HBTU to the Fmoc-Pro-Cys(Acm)-Cellulose.

The reaction was carried out as in step i. The synthesis cycle was programmed as follows.

| Step | Reagent | Time | Repeat | Volume | Activity |
|---|---|---|---|---|---|
| 1 | SOLV | 10 | X3 | 100 ml | WASHES SUPPORT |
| 2 | DEP | 10 min | X2 | 100 ml | DEP N-TERMINUS |
| 3 | SOLV | — | X6 | 100 ml | WASHES SUPPORT |
| 4 | ACT | 30 sec | X1 | 60 ml | DISSOLVES Fmoc-Trp |
| 5 | AA | 60 min | X1 | — | Fmoc-Trp COUPLING |
| 6 | SOLV | — | X3 | 100 ml | WASHES SUPPORT |

(iv) Synthesis of the Fmoc-Asp(OtBu)-Trp-Pro-Cys(Acm)-Cellulose by Coupling of the Fmoc-Asp(OtBu)/HBTU to the Fmoc-Trp-Pro-Cys(Acm)-Cellulose.

The reaction was carried out as in step i. The synthesis cycle was programmed as follows.

| Step | Reagent | Time | Repeat | Volume | Activity |
|---|---|---|---|---|---|
| 1 | SOLV | 10 | X3 | 100 ml | WASHES SUPPORT |
| 2 | DEP | 10 min | X2 | 100 ml | DEP N-TERMINUS |
| 3 | SOLV | — | X6 | 100 ml | WASHES SUPPORT |

-continued

| Step | Reagent | Time | Repeat | Volume | Activity |
|------|---------|------|--------|--------|----------|
| 4 | ACT | 30 sec | X1 | 60 ml | DISSOLVES Fmoc-Asp(O-t-Bu) |
| 5 | AA | 60 min | X1 | — | Fmoc-Asp (O-t-Bu) COUPLING |
| 6 | SOLV | — | X3 | 100 ml | WASHES SUPPORT |

(v) Synthesis of the Fmoc-Gly-Asp(OtBu)-Trp-Pro-Cys(Acm)-Cellulose by Coupling of the Fmoc-Gly/HBTU to the Fmoc-Asp(OtBu)-Trp-Pro-Cys(Acm)-Cellulose.

The reaction was carried out as in step i. The synthesis cycle was programmed as follows.

| Step | Reagent | Time | Repeat | Volume | Activity |
|------|---------|------|--------|--------|----------|
| 1 | SOLV | 10 | X3 | 100 ml | WASHES SUPPORT |
| 2 | DEP | 10 min | X2 | 100 ml | DEP N-TERMINUS |
| 3 | SOLV | — | X6 | 100 ml | WASHES SUPPORT |
| 4 | ACT | 30 sec | X1 | 60 ml | DISSOLVES Fmoc-Gly |
| 5 | AA | 60 min | X1 | — | Fmoc-Gly COUPLING |
| 6 | SOLV | — | X3 | 100 ml | WASHES SUPPORT |

(vi) Synthesis of the Fmoc-Lys(Boc)-Gly-Asp(O-t-Bu)-Trp-Pro-Cys(Acm)-Cellulose by Coupling of the Fmoc-Lys(Boc)/HBTU to the Fmoc-Gly-Asp(OtBu)-Trp-Pro-Cys(Acm)-Cellulose.

The reaction was carried out as in step i. The synthesis cycle was programmed as follows.

| Step | Reagent | Time | Repeat | Volume | Activity |
|------|---------|------|--------|--------|----------|
| 1 | SOLV | 10 | X3 | 100 ml | WASHES SUPPORT |
| 2 | DEP | 10 min | X2 | 100 ml | DEP N-TERMINUS |
| 3 | SOLV | — | X6 | 100 ml | WASHES SUPPORT |
| 4 | ACT | 30 sec | X1 | 60 ml | DISSOLVES Fmoc-Lys(Boc) |
| 5 | AA | 60 min | X1 | — | Fmoc-Lys (Boc) COUPLING |
| 6 | SOLV | — | X3 | 100 ml | WASHES SUPPORT |

(vii) Synthesis of the Mpr (Acm)-Lys(Boc)-Gly-Asp(OtBu)-Trp-Pro-Cys(Acm)-Cellulose by Coupling of the Mpr(Acm)/HBTU to Fmoc-Lys(Boc)-Gly-Asp(OtBu)-Trp-Pro-Cys(Acm)-Cellulose.

The reaction was carried out as in step i. The synthesis cycle was programmed as follows.

| Step | Reagent | Time | Repeat | Volume | Activity |
|------|---------|------|--------|--------|----------|
| 1 | SOLV | 10 | X3 | 100 ml | WASHES SUPPORT |
| 2 | DEP | 10 min | X2 | 100 ml | DEP N-TERMINUS |
| 3 | SOLV | — | X6 | 100 ml | WASHES SUPPORT |
| 4 | ACT | 30 sec | X1 | 60 ml | DISSOLVES Mpr (Acm) |
| 5 | AA | 60 min | X1 | — | Mpr(Acm) COUPLING |
| 6 | SOLV | — | X3 | 100 ml | WASHES SUPPORT |

Example (9)

Cleavage of the Peptide from the Cellulose Support to Yield Peptide Amide (Acm)Mpr-Lys-Gly-Asp-Trp-Pro-Cys(Acm)-CONH2       Formula (7)

The assembled peptidyl-cellulose support (from Example 8) is treated with 300 ml of the cleavage cocktail containing of TFA (95%): $H_2O$ (2.5%): TIS (2.5%): EDT (0%): Phenol (0%) for 2 hrs at ambient temperature in a glass stoppered 500 ml round bottom flask. The reaction mixture is filtered through G2 filter, and the TFA was evaporated on Rotavap. Precipitation of the peptide was carried out at −20° C. by addition of 300 ml of cold diisopropyl ether with the constant stirring. The crude peptide precipitate in the solvent is led to stand at −20° C. for 10 hrs. The peptide was isolated by filtering through Whatman paper no. 5, followed by cold solvent wash (100 ml×3) to remove the scavenger used in the cleavage cocktail. The crude peptide precipitate is dried under vacuum over $P_2O_5$, and characterized by RP-HPLC (FIG. 3). The Percentage Purity of the peptide obtained is more than 80%.

Example (10)

Guanylation of Crude Peptide to Yield (Acm)Mpr-Har-Gly-Asp-Trp-Pro-Cys(Acm)-$CONH_2$       Formula (8)

The peptide (1 g, 1.157 mmole) is dissolved in 15 ml of DMF, the pH adjusted to 9.0 with TEA. The reagent 3.5-dimethylpyrazole-1-carboxamidine nitrate (931.5 mg) in DMF (15 ml) is added to the peptide. The reaction mixture is stirred at 30° C. for 4 days with multiple additions of one time excess of reagent 3,5-dimethylpyrazole-1-carboxamidine nitrate.

The peptide is precipitated from the reaction mixture by the addition of 280 ml of acetonitrile (pH adjusted to 8.0 with TEA). The mix is further kept at −20° C. for 10 hrs. It is filtered through Whatman no. 5 filter paper and washed with acetonitrile (pH 8.0) 3 times, followed by plain acetonitrile to neutralize the pH. The precipitate is dried under high vacuum overnight. The peptide was characterized by RP-HPLC (FIG. 4). The yield of the peptide obtained is 85%.

Example (11)

DE-ACM of the Guanylated Peptide Followed by Oxidation to Yield

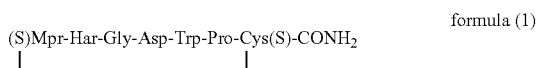

(S)Mpr-Har-Gly-Asp-Trp-Pro-Cys(S)-$CONH_2$       formula (1)

TFA (134.9 ml) and anisole (2.7 ml) are mixed, cooled in ice, added to 658 mg of pre-cooled peptide from example 3 and saturated with nitrogen. This is followed by addition of AgOTf (3.47 g) and stirred for 2 hrs in an ice bath. TFA is removed under high vacuum and silver salt of the peptide was precipitated by addition of diisopropyl ether (~400 ml). The reaction mixture is filtered through G-4 sintered funnel and precipitate (silver-peptide) is re-suspended in diisopropyl ether (60 ml×3), washed as above and dried over $P_2O_5$ under vacuum.

The oxidation of silver peptide is carried out by dissolving 10 mg of the silver-peptide salt in 15.6 ml of 50% DMSO/1M HCl in ice-cold condition. The reaction mixture is stirred for 3 hrs at 25° C. The precipitate is filtered through a G-4 sintered funnel or Hyflo bed to remove silver chloride. The filtrate is checked for completion of oxidation. On completion of the reaction crude peptide of formula (1) is obtained (FIG. 5). The Percentage Purity of the peptide obtained is 85%.

Example (12)

Purification of S—S Peptide

The crude disulfide looped peptide of formula (1) is loaded onto prep C-18 column (50×250 mm, 100 Å). The peptide is purified by using aqueous TFA (0.1%) and methanol in a gradient program. This is followed by an isocratic run using the above said solvent systems on a Shimadzu preparative HPLC System consisting of a controller, 2 LC8A pumps, UV-Vis detector. The purified peptide amide of formula (1) is analysed by analytical RP-HPLC (FIG. 6). The mass is determined by Mass Spectrophotometer (FIG. 7).

Example (13)

Purification of S—S Peptide

The purification was carried out in the same manner as Example 12, except that acetonitrile was used instead of methanol to obtain peptide amide of formula (1).

Example 14

Preparation of Acetate Salt of Formula (1)

The peptide of formula (1) as its TFA salt was loaded on to the column which was previously equilibrated with 0.1M 1M acetic acid buffer, preferably 0.1 to 0.5M and eluted with the equilabration buffer to isolate the peptide of formula(1) as the acetate salt in 99% purity. The column was selected from Sepharose Q, Sepharose DEAE, Sepharose AXN media.

The above-discussed sequences therefore have the following sequence listings:

SEQ. ID No. 1: Har-Gly-Asp-Trp-Pro-Cys 

SEQ. ID No. 2: Lys(Dde)-Gly-Asp(Otbu)-Trp-Pro-Cys
SEQ. ID No. 3: Lys-Gly-Asp(Otbu)-Trp-Pro-Cys
SEQ. ID No. 4: Har-Gly-Asp(Otbu)-Trp-Pro-Cys
SEQ. ID No. 5: Har-Gly-Asp-Trp-Pro-Cys
            |               |
           S—H        S—H SEQ. ID No. 6: Lys(Boc)-Gly-Asp(OtBu)-Trp-Pro-Cys
SEQ. ID No. 7: Lys-Gly-Asp-Trp-Pro-Cys
SEQ. ID No. 8: Har-Gly-Asp-Trp-Pro-Cys
SEQ. ID No. 9: Har-Gly-Asp-Trp-Pro-Cys
            |              |
           S—Ag      S—Ag

---

We claim:
1. A process for the preparation of a peptide N⁶-(aminoiminomethyl)-N²-(3-mercapto-1-oxopropyl-L-lysylglycyl-L-α-aspartyl-L-tryptophyl-L-prolyl-L-cysteinamide, cyclic (1→6)-disulfide of formula (1) on a solid support,

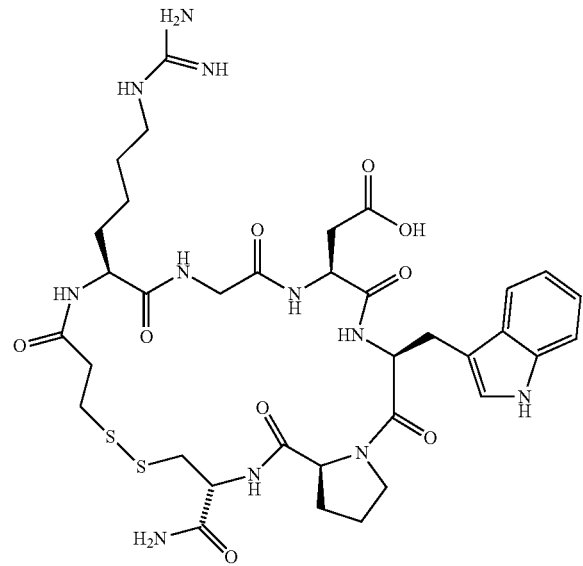

Formula (1)

said process comprising:
  a. assembling a peptide chain comprising of six amino acids and a thioalkyl carboxylic acid in a required sequence on a solid support to obtain a peptide bound resin of formula (2) as give below:

(Trt)Mpr-Lys (Dde)-Gly-Asp(Otbu)-Trp-Pro-Cys
     (Trt)-solid support           Formula (2);

b. capping the free amino groups after each coupling of (a) with acetic anhydride;
  c. cleaving Dde group in the peptide of formula (2) from the solid support to obtain peptide solid support of formula (3)

(Trt)Mpr-Lys-Gly-Asp(Otbu)-Trp-Pro-Cys(Trt)-solid
       support                    Formula (3);

d. guanylating the peptide of formula (3) at ε-lysine-NH₂ in an organic solvent to obtain peptide-solid support of formula (4) as given below:

(Trt)Mpr-Har-Gly-Asp(Otbu)-Trp-Pro-Cys(Trt)-solid
       support                    Formula (4);

e. cleaving and deprotecting all groups in the peptide of formula (4) from the solid support the obtain peptide-amide formula (5) as given below:

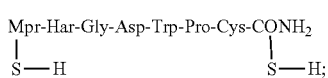

Formula (5)

f. oxidizing the SH-peptide of formula (5) with an appropriate oxidizing agent to obtain the crude peptide-amide of formula (1); and
  g. purifying the crude peptide-amide of formula (1) by chromatographic technique.

2. The process of claim 1, wherein the C-terminal of the protected first amino acid is bound to a solid support through a linker to obtain a solid support bound amine acid.

3. The process as claimed in claim 2, wherein the solid support is derivatised with rink amide linker.

4. The process of claim 1, wherein the solid support is either cellulose support or a resin support.

5. The process as claimed in claim 1, wherein the cellulose support is selected from a group consisting of cotton, gauze, fabric, paper and perloza beads.

6. The process as claimed in claim 1, wherein the amino acids used are selected from the group consisting of Cys, Pro, Trp, Asp, Gly, Lys, Arg, Har, Leu and Glu.

7. The process as claimed in claim 1, wherein the thioalkyl carboxylic acid used is mercapto propionic acid (Mpr).

8. The process as claimed in claim 1, wherein the organic solvent used for guanylation is selected from a group consisting of DMF, DCM, ethanol and methanol o mixture thereof.

9. The process as claimed in claim 1, wherein the guanylation is carried out using DMF.

10. The process as claimed in claim 1, the peptide is cleaved from solid support using the reagents TFA, TIS, EDT, DCM, Phenol and water in a defined ratio, preferably TFA (85-98%): TIS(0-5%): H₂O(0-5%): EDT(0-5%): Phenol(0-5%), more preferably TFA(94.5-95.5%): TIS(0-2.5%): H₂O (0-3%): EDT(0-2.5%).

11. The process as claimed in claim 1, wherein the precipitation is carried out by using a solvent selected from the group consisting of acetone, acetonitrile methanol, ethers, pentane and hexane or mixture thereof.

12. The process as claimed in claim 1, wherein the precipitation is carried out using diisopropyl ether.

13. The process as claimed in claim 1, wherein the peptide of formula (1) obtained has purity more than 99%.

14. The process as claimed in claim 1, wherein the peptide of formula (1) obtained is further converted into its acetate salt by ion-exchange chromatography.

15. An intermediate peptide of formula (2)

(Trt)Mpr-Lys(Dde)-Gly-Asp(Otbu)-Trp-Pro-Cys(Trt)-
     Solid support                Formula (2).

16. An intermediate peptide of formula (3)

(Trt)Mpr-Lys-Gly-Asp(Otbu)-Trp-Pro-Cys(Trt)-Solid
       support                    Formula (3).

17. An intermediate peptide of formula (4)

(Trt)Mpr-Har-Gly-Asp(Otbu)-Trp-Pro-Cys(Trt)-Solid
       support                    Formula (4).

* * * * *

SEQUENCE LISTING

```
<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: DISULFID
<222> LOCATION: (1)..(6)
<220> FEATURE:
<221> NAME/KEY: MOD_RES
<222> LOCATION: (1)..(1)
<223> OTHER INFORMATION: Homoarginine

<400> SEQUENCE: 1

Arg Gly Asp Trp Pro Cys
1               5

<210> SEQ ID NO 2
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)..(1)
<223> OTHER INFORMATION: 1-(4,4-dimethyl-2,6-dioxoyclohexylidene)ethyl
<220> FEATURE:
<221> NAME/KEY: MOD_RES
<222> LOCATION: (3)..(3)
<223> OTHER INFORMATION: O-t-butyl

<400> SEQUENCE: 2
```

```
Lys Gly Asp Trp Pro Cys
1               5

<210> SEQ ID NO 3
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (3)..(3)
<223> OTHER INFORMATION: O-t-butyl

<400> SEQUENCE: 3

Lys Gly Asp Trp Pro Cys
1               5

<210> SEQ ID NO 4
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)..(1)
<223> OTHER INFORMATION: Homoarginine
<220> FEATURE:
<221> NAME/KEY: MOD_RES
<222> LOCATION: (3)..(3)
<223> OTHER INFORMATION: O-t-butyl

<400> SEQUENCE: 4

Arg Gly Asp Trp Pro Cys
1               5

<210> SEQ ID NO 5
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)..(1)
<223> OTHER INFORMATION: Homoarginine
<220> FEATURE:
<221> NAME/KEY: DISULFID
<222> LOCATION: (1)..(6)

<400> SEQUENCE: 5

Arg Gly Asp Trp Pro Cys
1               5

<210> SEQ ID NO 6
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)..(1)
```

```
<223> OTHER INFORMATION: tert-butyloxycarbonyl
<220> FEATURE:
<221> NAME/KEY: MOD_RES
<222> LOCATION: (3)..(3)
<223> OTHER INFORMATION: O-t-butyl

<400> SEQUENCE: 6

Lys Gly Asp Trp Pro Cys
1               5

<210> SEQ ID NO 7
<211> LENGTH: 6
<212> TYPE: PRT
<213> ORGANISM: Artificial Sequence
<220> FEATURE:
<223> OTHER INFORMATION: completely synthesized

<400> SEQUENCE: 7

Lys Gly Asp Trp Pro Cys
1               5

<210> SEQ ID NO 8
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)..(1)
<223> OTHER INFORMATION: Homoarginine

<400> SEQUENCE: 8

Arg Gly Asp Trp Pro Cys
1               5

<210> SEQ ID NO 9
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: DISULFID
<222> LOCATION: (1)..(6)
<220> FEATURE:
<221> NAME/KEY: MOD_RES
<222> LOCATION: (1)..(1)
<223> OTHER INFORMATION: Homoarginine

<400> SEQUENCE: 9

Arg Gly Asp Trp Pro Cys
1               5
```